US00PP27916P3

(12) United States Plant Patent
Van Dijk

(10) Patent No.: US PP27,916 P3
(45) Date of Patent: Apr. 18, 2017

(54) ***ANTHURIUM* PLANT NAMED 'ANTHEOZO'**

(50) Latin Name: ***Anthurium andreanum* L.**
Varietal Denomination: ANTHEOZO

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 73 days.

(21) Appl. No.: 14/545,712

(22) Filed: Jun. 9, 2015

(65) Prior Publication Data

US 2016/0366804 P1 Dec. 15, 2016

(51) Int. Cl.
*A01H 5/02* (2006.01)

(52) U.S. Cl.
USPC ..... Plt./365

(58) Field of Classification Search
USPC ..... Plt./365, 369
See application file for complete search history.

(56) References Cited

PUBLICATIONS

Anthura unlimited in varieties *Anthurium* Cut flower & Pot plant culture 2014 retrieved on Oct. 12, 2016, retrieved from the Internet at <http://www.grenethplants.nl/images/brochures/ANTHURIUM.pdf> pp. 1, 32 and 47-48.*

Upov Pluto Plant Variety Database Sep. 24, 2016 retrieved on Oct. 12, 2016, retrieved from the Internet at <https://www3.wipo.int/pluto/user/en/index.jsp> one page.*

EU Community Plant Variety Rights Application No. 2013/1865, Application n°A201301369, filed Jul. 5, 2013, 7 pages.

EU Community Plant Variety Office Official Gazette, May 2013, Oct. 15, 2013, cover page and pp. 29, 48.

Anthura *Anthurium:* Cut flower and pot plant culture, published Nov. 2014, cover page and pp. 32, 47.

EU Community Plant Variety Rights Grant No. EU 41013, issued May 26, 2015, 2 pages.

Anthura *Anthurium* catalogue: Cut flower and pot plant 2015/2016, published May 2015, cover page and pp. 32, 39, 58.

* cited by examiner

*Primary Examiner* — June Hwu

(74) *Attorney, Agent, or Firm* — Jondle & Associates, P.C.

(57) ABSTRACT

A new and distinct variety of *Anthurium* plant named 'ANTHEOZO' particularly characterized by having a small, shiny, red, cordate spathe, a white spadix with a yellow tip, a compact plant habit and shiny, dark green foliage is disclosed.

3 Drawing Sheets

Genus and species: *Anthurium andreanum* L.
Variety denomination: 'ANTHEOZO'.

BACKGROUND OF THE NEW PLANT

The present invention comprises a new and distinct variety of *Anthurium*, botanically known as *Anthurium andreanum* L., and hereinafter referred to by the variety name 'ANTHEOZO'. The new variety originated from a hybridization made in August 2007 in Bleiswijk, The Netherlands. The female parent is a dark red *Anthurium* pot plant designated '6440-04' (unpatented), and the male parent was a red *Anthurium* plant designated '11283-17' (unpatented).

A single plant was selected in June 2009 and has been asexually reproduced repeatedly by meristem tissue culture in Bleiswijk, The Netherlands over a seven-year period. The present invention has been found to retain its distinctive characteristics through successive asexual propagations.

Plant Breeder's Rights for this variety have been applied for in the European Union on Jul. 5, 2013, in China on Jan. 29, 2015, and in Brazil on Apr. 20, 2015. 'ANTHEOZO' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Small, shiny, red, cordate spathe;
2) White spadix with yellow tip;
3) Compact plant habit; and
4) Shiny, dark green foliage.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 20-week old plant grown in a greenhouse in Bleiswijk, The Netherlands in April 2015.

DESCRIPTION OF THE NEW VARIETY

Figure 1:
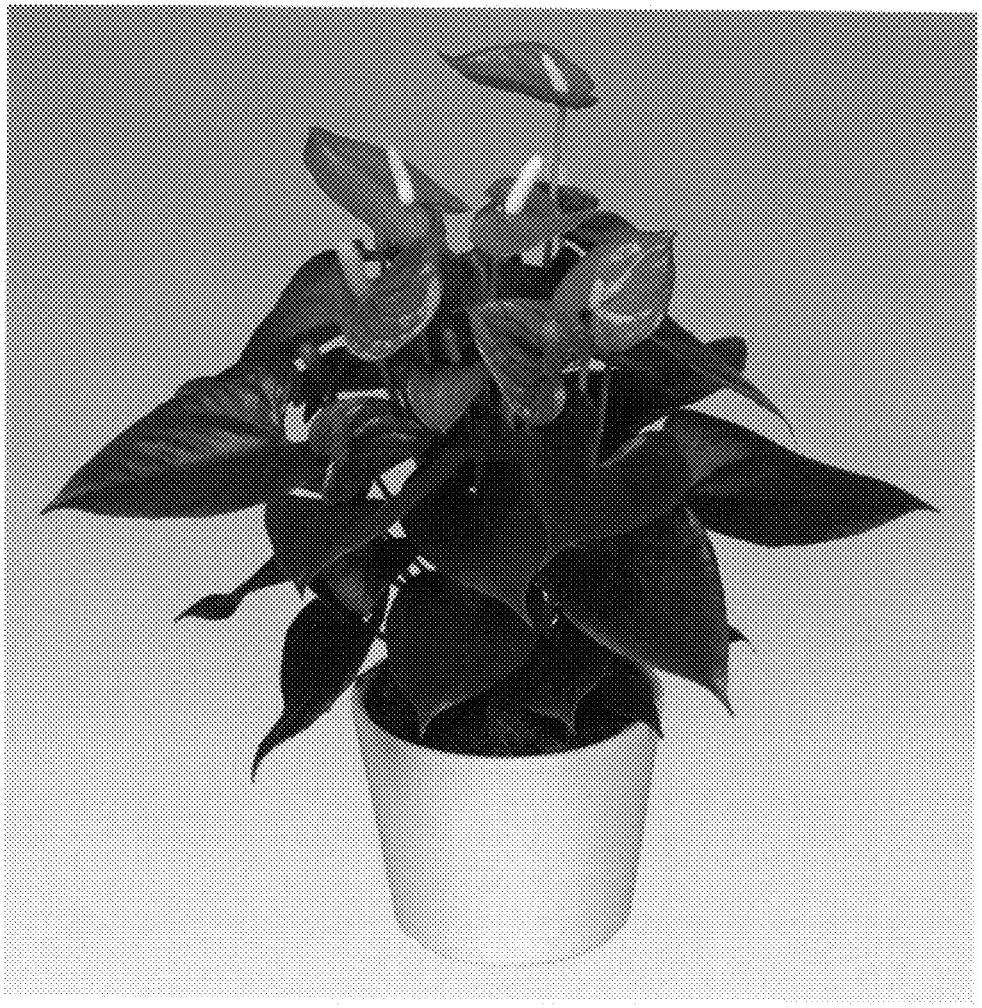
FIG. 1 shows the overall plant habit, including blooms and foliage.
Figure 2:
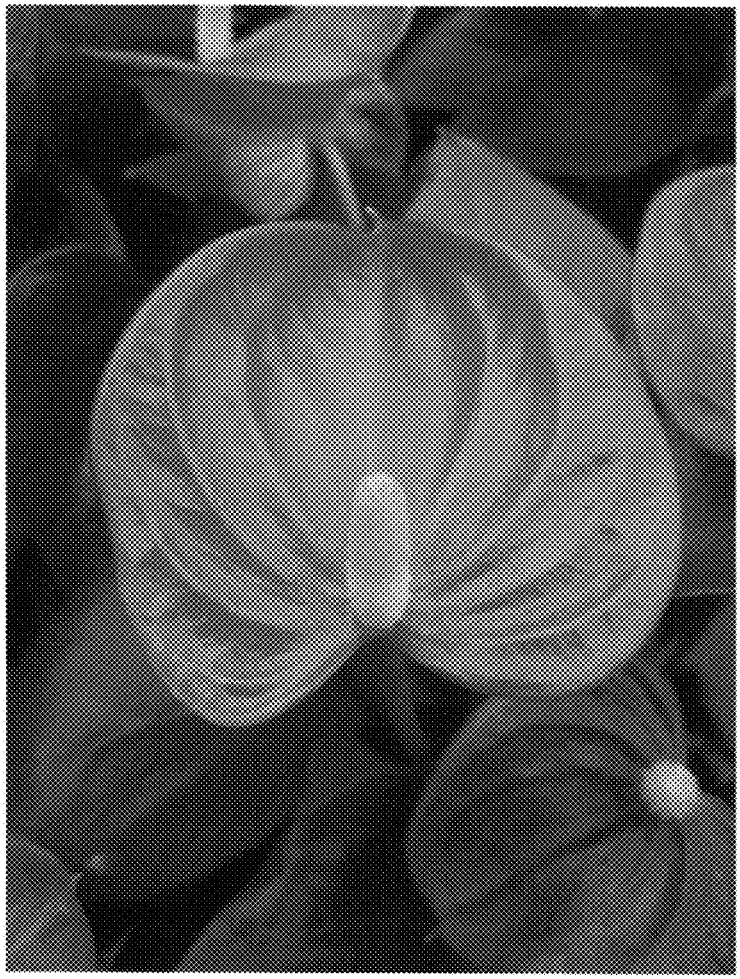
FIG. 2 shows a close-up of the mature spathe.
Figure 3:
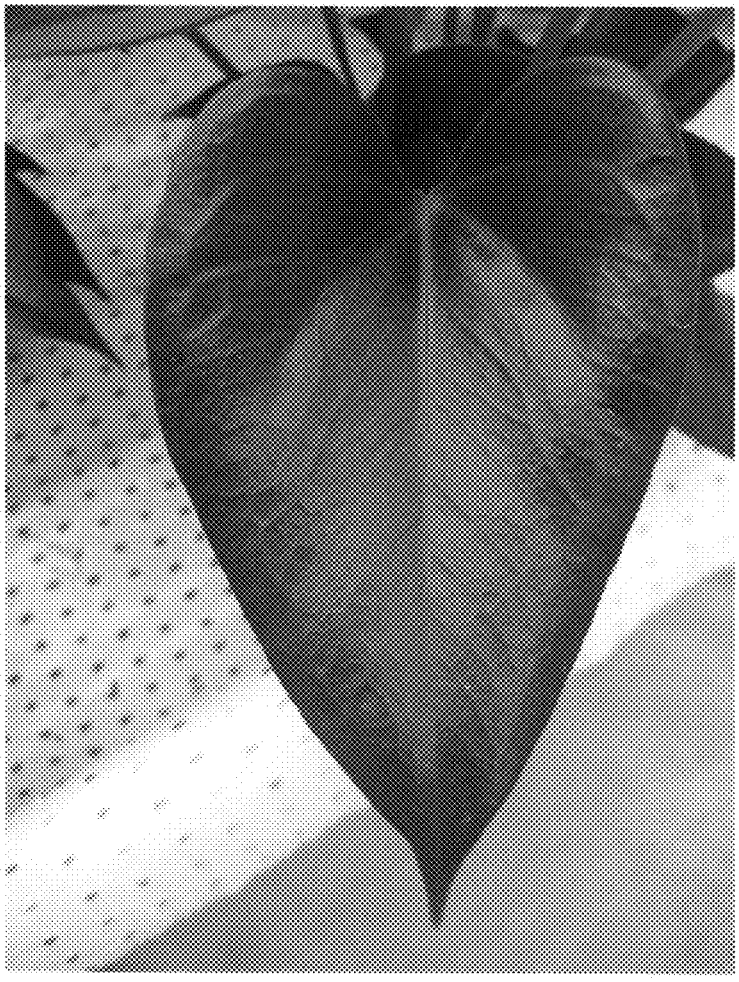
FIG. 3 shows the upper leaf blade surface.

The following detailed description sets forth the distinctive characteristics of 'ANTHEOZO'. The data which define these characteristics were collected from asexual reproductions carried out in Bleiswijk, The Netherlands. The plant history was taken on 20-week old plants which were planted from tissue culture in 9-centimeter pots and grown in a glass greenhouse between 19° C. and 24° C. Observations were made in April 2015. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHEOZO'.

Parentage:

*Female parent*.—*Anthurium* plant '6440-04' (unpatented).

*Male parent*.—*Anthurium* plant '11283-17' (unpatented).

Plant:

*Propagation*.—Meristem tissue culture.

*Root description*.—Fleshy white-cream colored roots with small hairy lateral roots having yellow-colored root tips.

*Time to produce a finished flowering plant*.—20 to 25 weeks for a 9 cm pot.

*Growth habit*.—Herbaceous perennial.

*Height* (*measured from soil, including inflorescence*).— 18.0 cm to 20.0 cm.

*Width* (*measured from leaf tips*).—23.0 cm to 25.0 cm.

Leaves:

*Immature leaves*.—Length: 8.0 cm to 11.0 cm. Width: 5.0 cm to 7.0 cm. Color: Upper surface: RHS 137A. Lower surface: RHS 146B. Texture (both upper and lower surfaces): Shiny.

*Mature leaves*.—Length (fully expanded): 8.0 cm to 12.0 cm. Width: 6.0 cm to 8.0 cm. Shape: Ovate-cordate. Apex: Acuminate. Base: Cordate. Leaf blade angle with the petiole: Between 90 degrees and 110 degrees. Leaf margin: Entire. Color: Upper surface: RHS 139A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Arrangement: Leaf blade has two lobes extending past the petiole. The lobes are non-touching. Length of lobes of mature leaf blades: 0.5 cm to 0.7 cm. Width of lobes of mature leaf blades: 3.0 cm to 3.5 cm. Distance for petiole/leaf junction to highest point on lobes of mature leaf blades: 2.0 cm to 2.5 cm.

*Petiole*.—Cross-section: Round. Diameter: 0.1 cm. Length: 7.0 cm to 9.0 cm for a mature leaf size. Color: Mature leaf: RHS 144A. Immature leaf: RHS 144A. Cataphyll color surrounding the petiole: Outside: RHS 144C. Inside: RHS 145C.

*Geniculum*.—Length: 1.5 cm to 2.0 cm. Width: 0.1 cm to 0.15 cm. Color: RHS 144A.

Inflorescence:

*Arrangement*.—Single.

*Flowering habit* (*length of flowering season*).—Continuous.

*Number of inflorescences per plant*.—4 to 5.

*Fragrance*.—Absent.

*Longevity of inflorescence on plant*.—Over a year.

*Longevity of the flower as a cut flower*.—45 to 55 days.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 90 degrees and 100 degrees; the spathe stands on a wiry peduncle about 2.0 cm to 4.0 cm above the foliage.

*Shape*.—Cordate.

*Apex*.—Broad acuminate.

*Base*.—Cordate.

*Texture*.—Shiny and slightly blistered.

*Margin*.—Entire.

*Size*.—Length: 5.0 cm to 6.0 cm. Width: 4.5 cm to 5.5 cm.

*Color*.—Just fully open: Upper surface: RHS 45A. Lower surface: RHS 45D. Mature: Upper surface: Red (RHS 45A). Lower surface: Red (RHS 45D). As it ages: Upper surface: Red (RHS 45A) and green (RHS 147A). Lower surface: Red (RHS 45D) and RHS 146A. When aging, veins green to RHS 147A, which gives the spathe a darker red appearance. Venation of immature spathe: Not visible. Venation of mature spathe: RHS 147A.

Peduncle:

*Shape*.—Erect.

*Cross-section*.—Round.

*Length*.—11.0 cm to 14.0 cm.

*Diameter*.—0.1 cm.

*Color*.—RHS 144B.

Flowering time:

*General*.—One small rooted untreated tissue culture plant of 2.0 cm tall will flower after 3 to 4 months, depending on the season, and 3 to 4 blossoms will appear. More blossoms appear after some additional weeks so that a full flowering and commercial plant will have 4 to 6 red spathes. Smaller blossoms may occur on less mature plants.

Spadix:

*Size*.—Length: 1.5 cm to 2.0 cm (depending on flower size). Width (at apex): 0.15 cm. Width (at base): 0.2 cm.

*Shape*.—Columnar.

*Angle from spadix tip to peduncle*.—170 to 180 degrees (spadix is almost in one line with the peduncle).

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 12A. Mature: RHS 159D. Ages to: Yellow green (RHS N144A and 151A) towards the tip; yellow (RHS 14A) tip (the spadix turns from yellow to green as it ages).

Flowers:

*Quantity per spadix.*—80 to 100.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 159D.

Reproductive organs:

*Stamens*.—Not visible.

*Pollen amount*.—Very few.

*Pollen color*.—RHS 156D.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 159D.

*Ovary*.—Rarely visible.

*Ovary color*.—Not measured.

Fruit and seed set: None observed.

Disease and pest resistance: Not observed to date.

COMPARISON WITH PARENTAL AND COMMERCIAL VARIETIES

'ANTHEOZO' differs from the female parent plant '6440-04' (unpatented) in that 'ANTHEOZO' has a red spathe, whereas '6440-04' has a dark red spathe.

'ANTHEOZO' differs from male parent plant '11283-17' (unpatented) in that 'ANTHEOZO' has a dark green immature leaf color, whereas '11283-17' has a more yellow/green immature leaf color.

'ANTHEOZO' differs from commercial variety 'ANTHEPEDI' (U.S. Plant Pat. No. 18,644) in that 'ANTHEOZO' has a longer spathe length and more narrow spathe width, whereas 'ANTHEPEDI' has a shorter spathe length and a broader spathe width. Additionally, 'ANTHEOZO' has an ovate-cordate leaf shape, whereas 'ANTHEPEDI' has an elliptical-cordate leaf shape.

'ANTHEOZO' differs from commercial variety 'ANTHDUNDAL' (U.S. Plant patent application Ser. No. 14/544,292) in that 'ANTHEOZO' has a smaller spathe length and width, whereas 'ANTHDUNDAL' has a larger spathe length and width. Additionally, 'ANTHEOZO' has an ovate-cordate leaf shape, whereas 'ANTHDUNDAL' has a long ovate leaf shape.

I claim:

1. A new and distinct variety of *Anthurium* plant named 'ANTHEOZO', substantially as illustrated and described herein.

* * * * *